United States Patent
Nakajima et al.

(10) Patent No.: US 8,642,618 B2
(45) Date of Patent: Feb. 4, 2014

(54) CARBOSTYRIL DERIVATIVES INCLUDING CILOSTAZOL FOR TREATING FATTY LIVER

(75) Inventors: Atsushi Nakajima, Yokohama (JP); Koji Fujita, Yokohama (JP); Masato Yoneda, Yokohama (JP); Osamu Mukeda, Osaka (JP); Takako Ichimura, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 426 days.

(21) Appl. No.: 12/667,875

(22) PCT Filed: Jul. 9, 2008

(86) PCT No.: PCT/JP2008/062771
§ 371 (c)(1),
(2), (4) Date: Oct. 20, 2010

(87) PCT Pub. No.: WO2009/008539
PCT Pub. Date: Jan. 15, 2009

(65) Prior Publication Data
US 2011/0039887 A1  Feb. 17, 2011

(30) Foreign Application Priority Data
Jul. 11, 2007 (JP) .................................. 2007-181760

(51) Int. Cl.
*A61K 31/4709* (2006.01)
*C07D 401/12* (2006.01)
*A61P 1/16* (2006.01)

(52) U.S. Cl.
USPC ............................ 514/312; 546/157; 546/158

(58) Field of Classification Search
USPC ................... 514/183, 312; 546/243, 157, 158
See application file for complete search history.

(56) References Cited

FOREIGN PATENT DOCUMENTS

JP   9-157170    6/1997
JP   3944257     4/2007

OTHER PUBLICATIONS

Yasunobu Matsuda, Kunio Matsumoto, Akira Yamada, Takafumi Ichida, Hitoshi Asakura, Yasunobu Komoriya, Eiji Nishiyama, and Toshikazu Nakamura, "Preventive and Therapeutic Effects in Rats of Hepatocyte Growth Factor Infusion on Liver Fibrosis/Cirrhosis", Hepatology vol. 26, No. 1, 1997, 81-89.*
Dohmen et al.—partial translation comment.*
International Preliminary Report on Patentability dated Jan. 21, 2010.
International Search Report from the European Patent Office in International Application No. PCT/JP2008/062771 mailed Sep. 15, 2008.
Fujita, et al., "Effectiveness of antiplatelet drugs against experimental non-alcoholic fatty liver disease", GUT online, XP009104963, pp. 1-19, (Jul. 2, 2008).
Fujita, et al., "Novel Therapeutic Approach for NAFLD Using Antiplatelet Agents in an Animal Model", Hepatology, vol. 46, No. 4, Suppl. S, XP-002493755, pp. 726-A to 763-A, (Oct. 2007).
Kosone, et al., "HGF ameliorates a high-fat diet-induced fatty liver", Am J Physiology—Gastrointestinal and Liver Physiology, vol. 293, No. 1, XP-002493822, pp. G204-G210, (Mar. 29, 2007).
Matsumoto, et al., "HGF: its organotrophic role and therapeutic potential", CIBA Foundation Symposium, vol. 212, XP-008005072, pp. 198-214, (Jan. 1, 1997).
Tahara, et al., Hepatocyte growth factor leads to recovery from alcohol-induced fatty liver in rats, Journal of Clinical Investigation, vol. 103, No. 3, XP-002493823, pp. 313-320, (Feb. 1999).
Kazufumi Dohmen et al., A case of Vasculo-Behcet's disease associated with fatty liver and pulmonary disease, KAN-TAN-SUI 36(5): 717-721, 1998.
Ribeiro, Paulo S. et al., Hepatocyte Apoptosis, Expression of Death Receptors, and Activation of NF-KB in the Liver of Nonalcoholic and Alcoholic Steatohepatitis Patients, Am. J. Gastroenterol., 2004, vol. 99, No. 9. p. 1708-1717.

* cited by examiner

*Primary Examiner* — Yong Chong
*Assistant Examiner* — Jason A Deck
(74) *Attorney, Agent, or Firm* — Finnegan, Henderson, Farabow, Garrett & Dunner, LLP

(57) ABSTRACT

The invention relates to a medicament for preventing and/or treating fatty liver which comprises as an active ingredient cilostazol or a pharmaceutically acceptable salt thereof.

2 Claims, 6 Drawing Sheets

CARBOSTYRIL DERIVATIVES INCLUDING CILOSTAZOL FOR TREATING FATTY LIVER

RELATED APPLICATIONS

This application is a §371 of International Application No. PCT/JP2008/062771, filed Jul. 9, 2008, which claims priority of Japanese Patent Application No. 2007-181760, filed Jul. 11, 2007, the contents of both of which are incorporated herein by reference.

TECHNICAL FIELD

The invention relates to a medicament for preventing and/or treating fatty liver. More particularly, it relates to a medicament for preventing and/or treating fatty liver which comprises as an active ingredient a carbostyril derivative of formula (1):

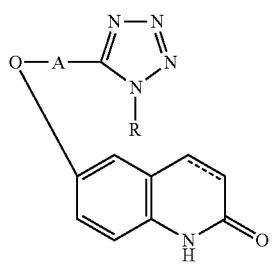

(1)

wherein A is a lower alkylene group, R is a cycloalkyl group, the bonding between 3- and 4-positions of the carbostyril skeleton is a single bond or a double bond, or a salt thereof.

BACKGROUND ART

The carbostyril derivatives of formula (1) or salts thereof and the process for the preparation thereof are disclosed in JP-63-20235-B. And it is known that the carbostyril derivatives (1) have platelet aggregation inhibitory action, phosphodiesterase (PDE) inhibition action, antiulcer, hypotensive action and antiphlogistic action, and are useful as an antithrombotic agent, a drug for improving cerebral circulation, an antiinflammatory agent, an antiulcer drug, an antihypertensive drug, an antiasthmatic drug, a phosphodiesterase inhibitor, etc.

In addition, JP-9-157170-A reports that the carbostyril derivative may be useful as an agent for promoting hepatocyte growth factor (HGF) production. Therefore, the hepatocyte growth action thereof is expected to be useful in the case of treating a disease such as fulminant hepatic failure or promoting the liver regeneration after hepatectomy.

These days, an interest in metabolic syndrome has been increasing. With regard to the evaluation of the syndrome, visceral fat is adopted as one of the criteria thereof. Amongst the visceral fat, especially an interest in fatty liver is increasing. Fatty liver is in a condition that fat is built up in the liver, which causes little subjective symptom. However, the condition could get worse when left untreated, and not a few patients suffering from fatty liver may progress in hepatitis, cirrhosis and liver cancer.

Fatty liver can be roughly classified into alcoholic fatty liver and non-alcoholic fatty liver. As patients of metabolic syndrome increase, there is increasing interest in non-alcoholic steatohepatitis (NASH) in Japan that is a disease of fatty liver accompanied with symptoms of necrosis of hepatocyte, inflammation, and/or fibril formation, which affects even non-drinkers. Although the cause of NASH has not been sufficiently clarified yet, it is thought that fatty liver may be one of the causes at least. Therefore, a strict nutrition therapy is important for the treatment thereof, and drug therapy is also considered for intractable symptom (M. Yoneda, et al., *Folia Pharmacologica Japonica*, Vol. 128 (2006), No. 4 235-238).

Thus, fatty liver has seriously critical factors to progress toward severe cases, however, there are few effective medicaments for preventing and treating fatty liver. It has been still desired to develop an effective medicament for fatty liver, especially NASH whose cause has not been sufficiently clarified yet and non-alcoholic fatty liver which might progress toward NASH.

DISCLOSURE OF INVENTION

As mentioned above, no satisfied medicament for preventing and treating fatty liver has been found yet, and thus it has been desired to develop a medicament for preventing and treating fatty liver in Japan and other countries. In addition, there has been no/few medicament for treating NASH because NASH is a newly uprising disease. Furthermore, the condition of NASH is thought to be composed of a variety of factors which are complicatedly related, and thus it is not enough to treat the disease with a single medicament, and usually plural medicaments must be used for the treatment. From the viewpoint of the need for treating this new disease, NASH, it has been desired to develop a new medicament for the treatment or apply an existent medicament to the treatment.

The present inventors have intensively studied a new medicament for preventing and/or treating fatty liver and have found that a carbostyril derivative of the above formula (1), especially 6-[4-(1-cyclohexyl-1H-tetrazol-5-yl)butoxy]-3,4-dihydrocarbostyril (cilostazol) or a salt thereof is useful for preventing and/or treating fatty liver. As mentioned above, it has been already known that the carbostyril derivative has a hepatocyte growth action as an agent for promoting HGF, however, it is very surprising and unexpected from the mechanistic viewpoint that the derivative may be used for treating fatty liver though the target organ of both the diseases is the same liver.

The present inventors have found for the first time that 6-[4-(1-cyclohexyl-1H-tetrazol-5-yl)butoxy]-3,4-dihydro-carbostyril (cilostazol) or a salt thereof could improve the treatment of fatty liver on model animals suffering from fatty liver, and then have accomplished the present invention.

The present invention provides a medicament for preventing and/or treating fatty liver comprising as an active ingredient a carbostyril derivative of the general formula:

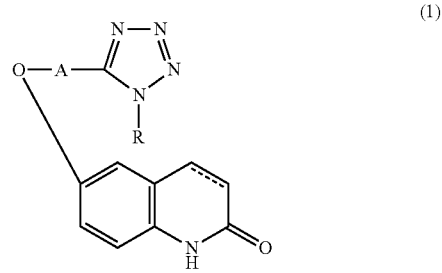

(1)

wherein A is a lower alkylene group, R is a cycloalkyl group, the bonding between 3- and 4-positions of the carbostyril skeleton is a single bond or a double bond, or a salt thereof.

The present invention also provides a medicament for preventing and/or treating fatty liver comprising as an active ingredient 6-[4-(1-cyclohexyl-1H-tetrazol-5-yl)butoxy]-3,4-dihydrocarbostyril (cilostazol) or a salt thereof.

The present invention also provides a composition for preventing and/or treating fatty liver comprising the above-mentioned carbostyril derivative (1).

The present invention also provides use of the above-mentioned carbostyril derivative (1) in preparation of a medicament for preventing and/or treating fatty liver.

The present invention also provides a method for preventing and/or treating fatty liver which comprises administering an effective amount of the above-mentioned carbostyril derivative (1) to a patient in need thereof.

According to the present invention, 6-[4-(1-cyclohexyl-1H-tetrazol-5-yl)butoxy]-3,4-dihydrocarbostyril (cilostazol) or a salt thereof may be useful for preventing/treating NASH through preventing and/or treating fatty liver and inhibiting the initial stage of NASH. Furthermore, the invention provides a medicament for preventing and/or treating NASH comprising as an active ingredient the above-mentioned carbostyril derivative (1).

BEST MODE FOR CARRYING OUT THE INVENTION

Figure 1:
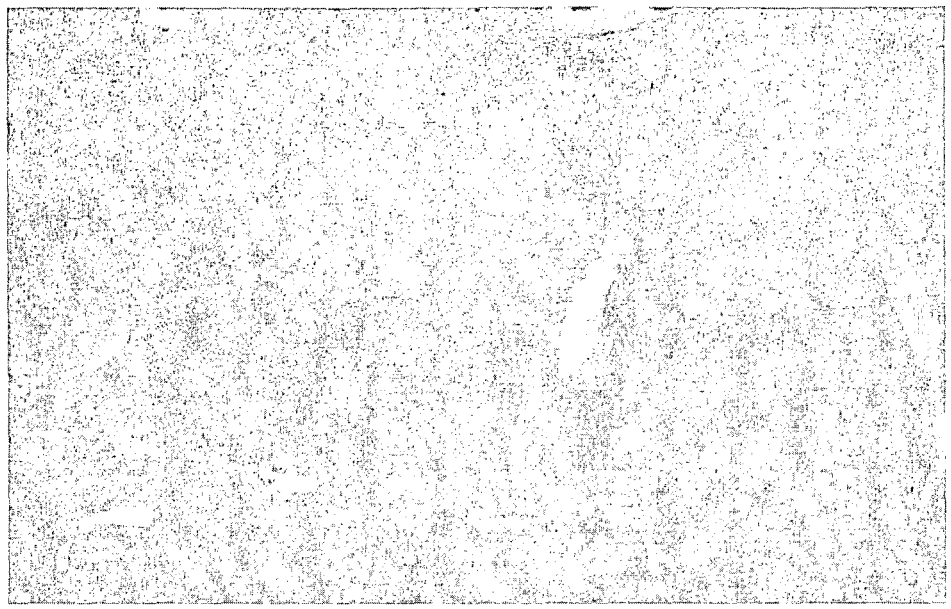
FIG. 1 shows the result of the Hematoxylin-eosin-stained liver in the control group rats to which only a general diet was given for 6 weeks.
Figure 2:
FIG. 2 shows the result of the Hematoxylin-eosin-stained liver in the CDAA group rats to which the CDAA diet was given for 6 weeks.
Figure 3:
FIG. 3 shows the result of the Hematoxylin-eosin-stained liver in the cilostazol-administration group rats to which the CDAA diet+6 mg/kg of cilostazol was given every day for 6 weeks.
Figure 4:
FIG. 4 shows the result of the Hematoxylin-eosin-stained liver in the aspirin-administration group rats to which the CDAA diet+5 mg/kg of aspirin was given every day for 6 weeks.
Figure 5:
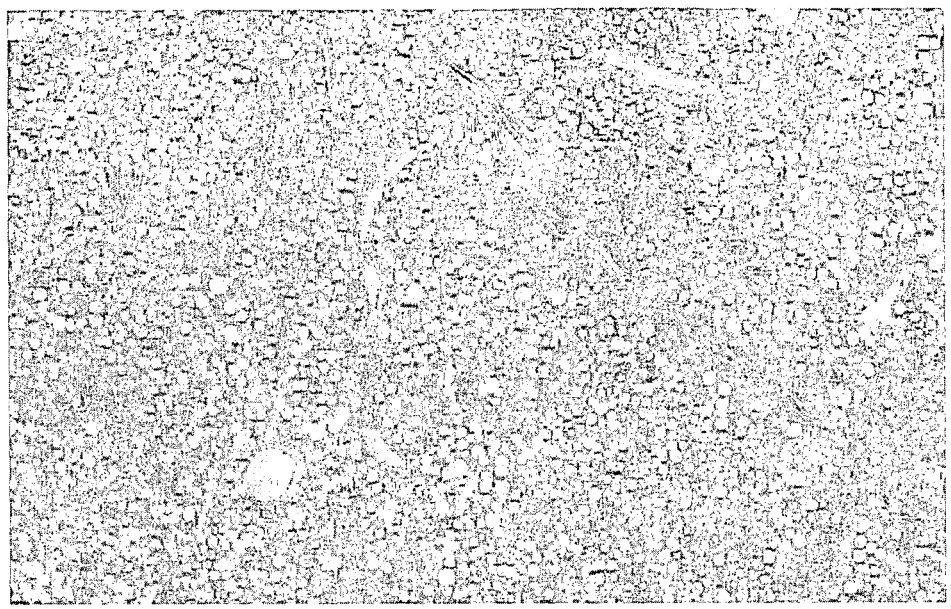
FIG. 5 shows the result of the Hematoxylin-eosin-stained liver in the ticlopidine-administration group rats to which the CDAA diet+10 mg/kg of ticlopidine was given every day for 6 weeks.
Figure 6:
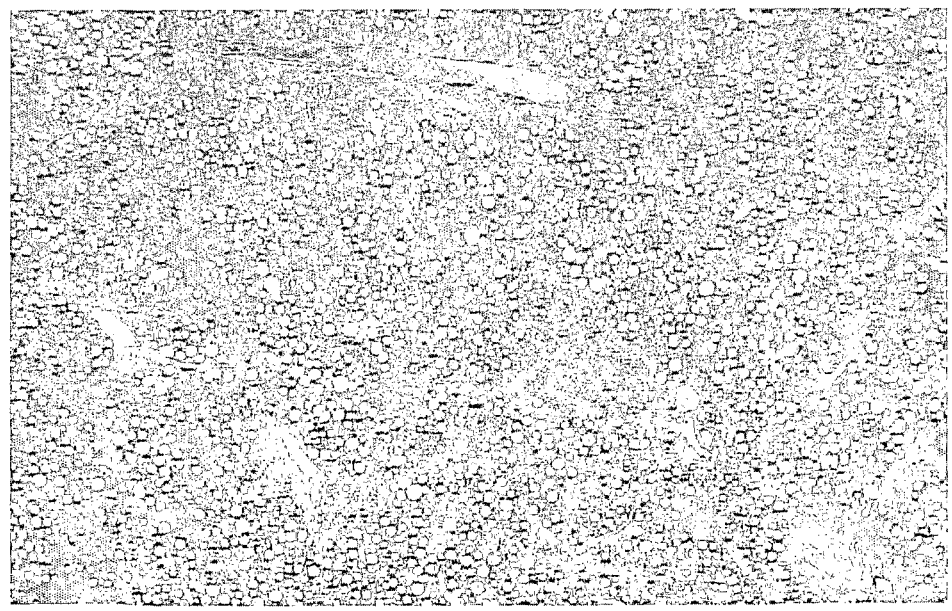
FIG. 6 shows the result of the Masson-stained liver in the CDAA group rats to which the CDAA diet was given for 6 weeks.
Figure 7:
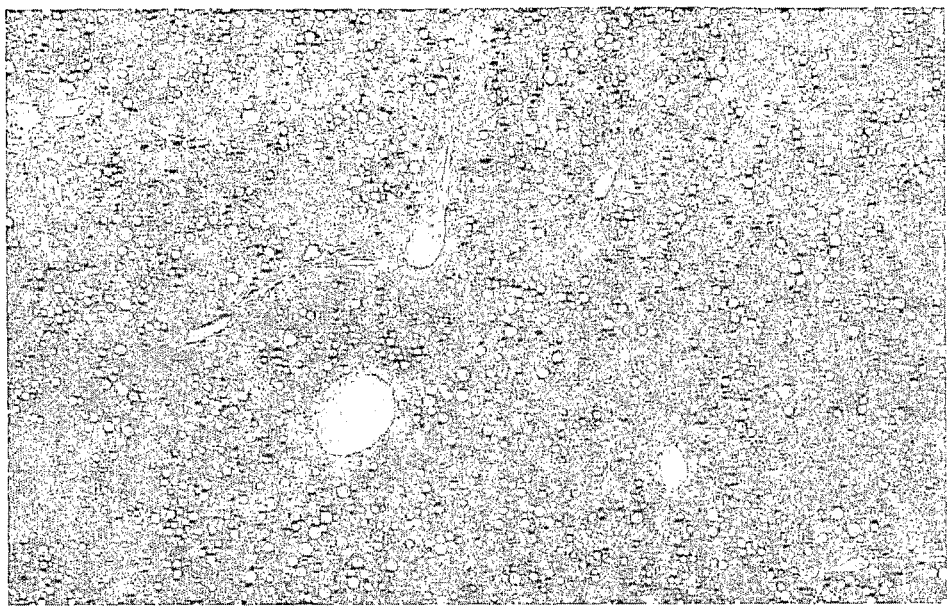
FIG. 7 shows the result of the Masson-stained liver in the cilostazol-administration group rats to which the CDAA diet+6 mg/kg of cilostazol was given every day for 6 weeks.
Figure 8:
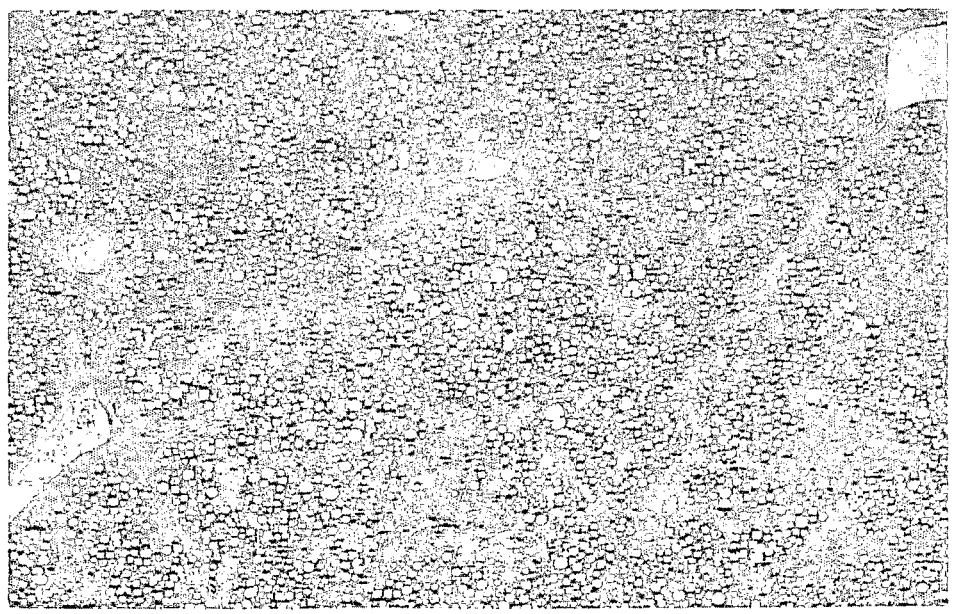
FIG. 8 shows the result of the Masson-stained liver in the aspirin-administration group rats to which the CDAA diet+5 mg/kg of aspirin was given every day for 6 weeks.
Figure 9:
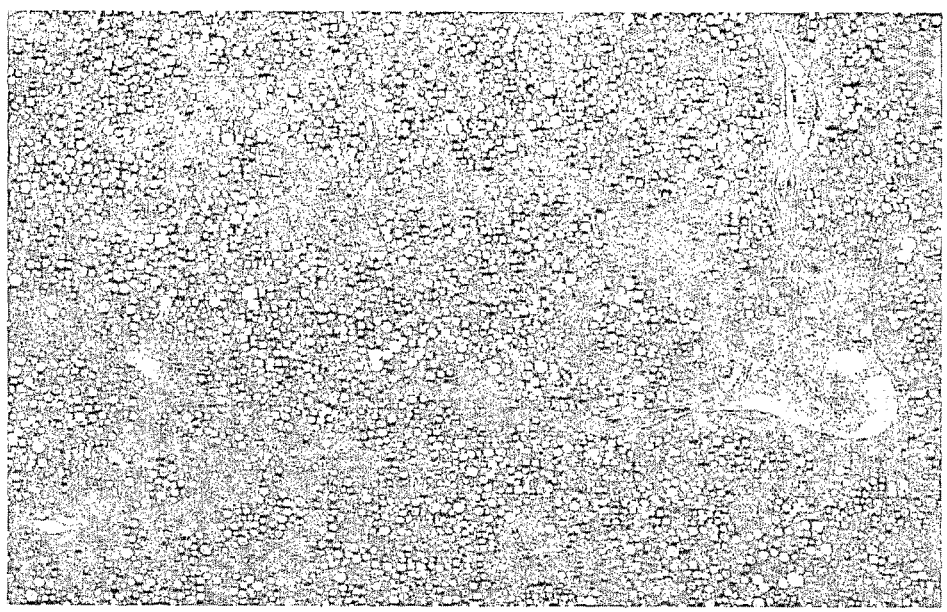
FIG. 9 shows the result of the Masson-stained liver in the ticlopidine-administration group rats to which the CDAA diet+10 mg/kg of ticlopidine was given every day for 6 weeks.

In the above carbostyril derivative (1), the cycloalkyl group includes $C_3$-$C_8$ cycloalkyl groups such as cyclopropyl, cyclobutyl, cyclopentyl, cyclohexyl, cycloheptyl, and cyclooctyl. Preferred cycloalkyl group is cyclohexyl. The lower alkylene group includes $C_1$-$C_6$ alkylene groups such as methylene, ethylene, propylene, butylene, and pentylene, among which preferred one is butylene.

Preferable carbostyril derivative (1) is 6-[4-(1-cyclohexyl-1H-tetrazol-5-yl)butoxy]-3,4-dihydrocarbostyril, which has been put on the market in the trade name of cilostazol as an antiplatelet agent.

The carbostyril derivative (1) can be easily converted to a salt thereof by getting it treated with a pharmaceutically acceptable acid. The acid includes, for example, inorganic acids such as hydrochloric acid, sulfuric acid, phosphoric acid, and hydrobromic acid; and organic acids such as oxalic acid, maleic acid, fumaric acid, malic acid, tartaric acid, citric acid, and benzoic acid.

These carbostyril derivatives (1) and salts thereof and processes for preparation thereof are disclosed in JP-63-20235-B.

The carbostyril derivatives of formula (1) may be used in bulk or preferably in the form of a pharmaceutical preparation with a conventional pharmaceutical carrier or diluent. The dosage form in the present invention includes, but not limited thereto, for example, the dosage forms exemplified in JP-10-175864-A, and typically an oral solid dosage form such as tablets, capsules, and particles; various liquid preparations suitable for oral administration; and also a parenteral preparations such as injections and suppositories. The dose of the carbostyril derivative (1) is not limited to a specific range. The carbostyril derivatives (1) or a salt thereof may be used in an amount of 100 to 400 mg/day per an adult (50 kg of body weight), which is administered once a day or two to several times per day. The carbostyril derivative (1) may be included in 0.1-70% (w/w) per the composition of the preparation, preferably 50-100 mg per a dosage unit of the preparation.

The preparation for injection is usually prepared in the form of a liquid preparation, an emulsion, or a suspension, which are sterilized and further are preferably made isotonic to the blood. The preparations in the form of liquid, emulsion or suspension are usually prepared by using conventional pharmaceutical diluents such as water, ethyl alcohol, propylene glycol, ethoxylated isostearyl alcohol, polyoxylated isostearyl alcohol, and polyoxyethylene sorbitan fatty acid esters. These preparations may be prepared by mixing the carbostyril derivative (1) with an isotonic agent such as sodium chloride, glucose, glycerin in an amount sufficient for making isotonic and may further be prepared by mixing with conventional solubilizers, buffers, anesthetizing agents, and optionally colorants, preservatives, fragrant materials, flavors, sweetening agents, and other medicaments.

The preparations of the invention such as tablets, capsules, liquid for oral administration may be prepared by a conventional method. The tablets may be prepared by mixing the carbostyril derivative (1) with conventional pharmaceutical carriers such as gelatin, starches, lactose, magnesium stearate, talc, gum arabic, and the like. The capsules may be prepared by mixing the carbostyril derivative (1) with inert pharmaceutical fillers or diluents and filling hard gelatin capsules or soft capsules with the mixture. The oral liquid preparations such as syrups or elixirs are prepared by mixing the carbostyril derivative (1) with sweetening agents (e.g. sucrose), preservatives (e.g. methylparaben, propylparaben), colorants, flavors, and the like. The preparations for parenteral administration may also be prepared by a conventional method, for example, by dissolving the carbostyril derivative (1) of the present invention in a sterilized aqueous carrier, preferably water or a saline solution. Preferred liquid preparation suitable for parenteral administration is prepared by dissolving about 50-100 mg of the carbostyril derivative (1) in water and an organic solvent and further in a polyethylene glycol having a molecular weight of 300 to 5000, in which preferably a lubricant such as sodium carboxymethylcellulose, methylcellulose, polyvinylpyrrolidone, and polyvinyl alcohol may be incorporated. Preferably, the above liquid preparations may further comprise a disinfectant (e.g. benzyl alcohol, phenol, thimerosal), a fungicide, and further optionally an isotonic agent (e.g. sucrose, sodium chloride), a topical anesthetic, a stabilizer, a buffer, and the like. In view of keeping stability, the preparation for parenteral administration may be put in a capsule, followed by removing the aqueous medium by a conventional lyophilizing technique. The preparation can be recovered into a liquid preparation by dissolving it in an aqueous medium when used.

EXAMPLE

Fisher 344 rats were fed only a general diet or a choline-deficiented, L-amino acid-defined (CDAA) diet to prepare a control group and a CDAA group as an animal model for fatty liver, respectively. Three medicament-treated groups were prepared by administering the following three medicaments to the CDAA groups every day. (Aspirin and ticlopidine are medicaments having the same platelet aggregation inhibitory action as cilostazol.)

6 mg/kg of cilostazol
    5 mg/kg of aspirin
    10 mg/kg of ticlopidine

Figure 10:
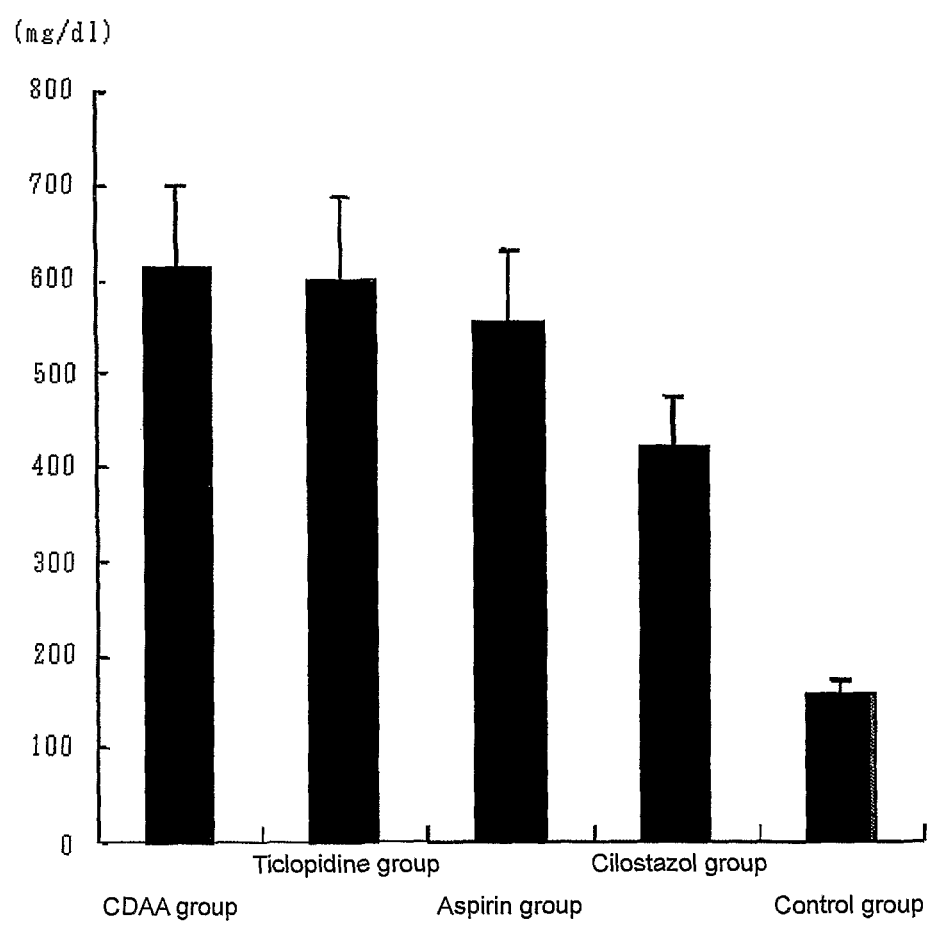
FIG. 10 shows serum level of triglyceride in each rat of the CDAA group, the ticlopidine-administration group, the aspirin-administration group, the cilostazol-administration group, and the control group, which was 6 weeks after the administration of medicaments started.

Six weeks after the administration of medicaments started, livers of the rats in each medicament-treated group were taken out and stained with Hematoxylin-eosin staining and Masson staining, in which lipid droplets were observed. The results of the Hematoxylin-eosin staining are shown in FIG. 1-FIG. 5, and the results of the Masson staining are shown in FIG. 6-FIG. 9. According to these results, the lipid droplet of liver in the cilostazol-administration group (i.e. administered 6 mg/kg of cilostazol+CDAA) was markedly less than that of the CDAA group without cilostazol administration or that of the aspirin/ticlopidine administration groups. In addition, the amount of triglyceride in the liver as well as the serum level of triglyceride in those rats were measured. The serum levels of triglyceride in each rat of every groups are shown in FIG. 10. As is seen from the results, it was found that the serum level of triglyceride in the cilostazol-administration (6 mg/kg) group was significantly lower than that in the control group and in other medicaments-treated groups. Therefore, it was found that cilostazol is a useful medicament for the prevention and/or treatment of fatty liver.

The invention claimed is:

1. A method for treating fatty liver in a patient with non-alcoholic steatohepatitis (NASH) which comprises administering as an active ingredient an effective amount of a carbostyril derivative or a salt of the following formula to a patient in need thereof:

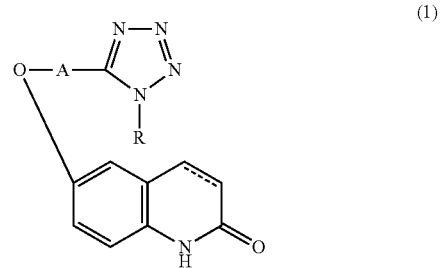

wherein A is a lower alkylene group, R is a cycloalkyl group and the bonding between 3- and 4-positions of the carbostyril skeleton is a single bond or a double bond.

2. The method of claim 1 wherein the active ingredient is 6-[4-(1-cyclohexyl-1H-tetrazol-5-yl)butoxy]3,4-dihydrocarbostyril or a salt thereof.

\* \* \* \* \*